United States Patent
Santus et al.

(10) Patent No.: US 9,980,975 B2
(45) Date of Patent: May 29, 2018

(54) DOSAGE FORMS CONTAINING FLUTICASONE PROPIONATE FOR THE TREATMENT OF INFLAMMATORY CONDITIONS OF THE ESOPHAGUS

(71) Applicant: EMS S.A., São Paulo (BR)

(72) Inventors: Giancarlo Santus, Milan (IT); Leticia Khater Covesi, São Paulo (BR); Luca Donadoni, Alzano Lombardo (IT); Christina Ecclissato, São Paulo (BR); Roberto Amazonas, São Paulo (BR)

(73) Assignee: EMS S.A., São Paulo (BR)

( * ) Notice: Subject to any disclaimer, the term of this patent is extended or adjusted under 35 U.S.C. 154(b) by 0 days. days.

(21) Appl. No.: 14/603,224

(22) Filed: Jan. 22, 2015

(65) Prior Publication Data
US 2016/0213681 A1 Jul. 28, 2016

(51) Int. Cl.
| | | |
|---|---|---|
| *A61K 31/56* | (2006.01) | |
| *A61K 47/36* | (2006.01) | |
| *A61K 47/38* | (2006.01) | |
| *A61K 47/26* | (2006.01) | |
| *A61K 47/14* | (2017.01) | |
| *A61K 47/32* | (2006.01) | |
| *A61K 9/00* | (2006.01) | |

(52) U.S. Cl.
CPC ............ *A61K 31/56* (2013.01); *A61K 9/0095* (2013.01); *A61K 47/14* (2013.01); *A61K 47/26* (2013.01); *A61K 47/32* (2013.01); *A61K 47/36* (2013.01); *A61K 47/38* (2013.01)

(58) Field of Classification Search
None
See application file for complete search history.

(56) References Cited

U.S. PATENT DOCUMENTS

| | | | | |
|---|---|---|---|---|
| 6,251,371 | B1 * | 6/2001 | Holmen | A61K 8/34 424/49 |
| 2009/0123550 | A1 | 5/2009 | Phillips et al. | |
| 2010/0216754 | A1 * | 8/2010 | Hill | A61K 9/006 514/171 |
| 2012/0323178 | A1 * | 12/2012 | Padilla | A61K 9/0043 604/151 |

FOREIGN PATENT DOCUMENTS

| | | |
|---|---|---|
| GB | 2 088 877 A | 6/1982 |
| WO | WO 2004/069225 A1 | 8/2004 |
| WO | WO 2011/041509 A1 | 4/2011 |

OTHER PUBLICATIONS

Geraghty et al., "An invesitgaiton of the parameters influencing the bioadhesive properties of Myverol 18-99/water gels," Biomaterials 18 (1997) 63-67.*

Ahmed et al., Formulation and Evaluation of Gastric-Mucoadhesive Drug Delivery Systems of Captopril, JCPR 2010; 2(1): 26-32.*

Chakraborty et al., "Fabrication and Characterization of Algino-Carbopol Microparticulate System of Aceclofenac for Oral Sustained Release Drug Delivery," International Journal of Pharmaceutical Sciences Review and Research, vol. 4, Issue 2, Sep.-Oct. 2010.*

* cited by examiner

*Primary Examiner* — Jared D Barsky
(74) *Attorney, Agent, or Firm* — Arent Fox LLP

(57) ABSTRACT

The present invention describes novel and improved dosage forms containing fluticasone propionate for the treatment of conditions associated with inflammation of the esophagus.

1 Claim, No Drawings

DOSAGE FORMS CONTAINING FLUTICASONE PROPIONATE FOR THE TREATMENT OF INFLAMMATORY CONDITIONS OF THE ESOPHAGUS

FIELD OF THE INVENTION

This invention relates to improved dosage forms of a steroid, for the treatment of inflammatory conditions of the esophagus. In particular the present invention relates to pharmaceutical compositions of fluticasone propionate with good bioavailability, reduced side effects, enhanced patient compliance, and a method for obtaining said improved dosage forms for the treatment of eosinophilic esophagitis.

BACKGROUND

Eosinophilic esophagitis is an allergic inflammatory disease characterized by elevated eosinophils in the esophagus. This inflammatory condition of the esophagus affects both children and adults, and men more than women.

Eosinophilic esophagitis is a newly recognized disease that over the past decade has been increasingly diagnosed. It is a rare disease, but increasing in prevalence to an estimated 1:2000. This increase is thought to reflect an increase in diagnosis, as well as a true increase in eosinophilic esophagitis cases. Fortunately, the medical community is responding and new scientific information is emerging to guide management of this disorder, which often persists with ongoing or recurrent symptoms.

The major symptom in adults with eosinophilic esophagitis is dysphagia (problems of swallowing) for solid food. Eosinophilic esophagitis stiffens the esophagus so that solid foods have difficulty passing through the esophagus into the stomach. Other common causes of dysphagia for solid food are esophageal strictures and Schatzki rings. The diagnosis of eosinophilic esophagitis usually is made during an endoscopy (EGD), performed for the evaluation of dysphagia and is confirmed by biopsy of the esophagus.

People with eosinophilic esophagitis commonly have other allergic diseases such as rhinitis, asthma, and/or eczema. Eosinophilic esophagitis can be driven by food allergy or intolerance: most patients who eliminate food proteins from their diet (by drinking only an amino-acid based formula) improve. The disease may also be triggered by other environmental factors that researchers are beginning to understand.

There are a number of studies that have demonstrated the central role of food allergens in triggering eosinophilic esophagitis. When these allergenic foods are removed from a person's diet, symptoms can resolve and the eosinophilic inflammation in the esophagus can be healed.

In addition, there are medical therapies available—the most common drug therapy is the use of swallowed inhaled steroids such as budesonide (Pulmicort) made into a slurry or fluticasone (Flovent) inhalers. Presently these therapies are off-label treatments as there no approved drug medications with this clinical indication.

The selected steroid of this invention is fluticasone propionate, a compound with potent anti-inflammatory activity widely used for the treatment of respiratory diseases.

Fluticasone propionate is an old drug described firstly in British Patent 2088877. There are several different dosage forms commercially available, such as oral tablets, inhalation dry powders, oral inhalation aerosol, nasal sprays, topical dermatological cream and ointments etc.

Novel fluticasone formulations with at least one surface stabilizer and particle size of less than about 2000 nm are described in WO2004/069225. The formulations described in this patent are mainly for treating respiratory related illness. There is no mention of gastrointestinal diseases in general nor, specifically, of eosinophilic esophagitis.

Orally administered corticosteroid compositions are described in WO2011/041509. This application is primarily directed to solid dispersible dosage forms also in presence of bioadhesive polymers. There are described moreover liquid bioadhesive formulations, mainly non aqueous. There is no mention of viscous sugar free aqueous liquid formulations of fluticasone propionate.

None of the known prior art describes a viscous sugar free liquid formulation of fluticasone propionate specifically designed for treatment of eosinophilic esophagitis.

There is therefor a need in the art for orally administered steroid formulations specifically designed for the treatment of eosinophilic esophagitis that can decrease frequency of administration, improve clinical efficacy and reduce side effects associated with the use of steroids.

SUMMARY OF THE INVENTION

One embodiment of the present invention is a liquid composition of fluticasone propionate.

In another embodiment the present invention is directed to a sugar free liquid fluticasone propionate formulation.

In another embodiment the formulation is a high viscosity formulation to enhance the contact time with the esophageal mucosa.

In another embodiment is directed to a liquid viscous composition comprising sodium alginate.

Another embodiment is directed to a viscous liquid dosage form comprising fluticasone propionate in combination with sodium alginate and other non-active ingredients.

In another embodiment, the present invention is directed to a process for the preparation of a dosage form containing fluticasone propionate and sodium alginate.

In yet another embodiment the present invention is directed to a method of treating eosinophilic esophagitis.

DESCRIPTION OF THE INVENTION

The present invention provides pharmaceutical compositions of fluticasone propionate for oral administration wherein said compositions provide a better patient treatment with good bioavailability, good tolerability and improved compliance by increase in viscosity of the compositions and reduction of number of administrations.

In particular, the present invention deals with formulations comprising fluticasone propionate and sodium alginate in the form of viscous sugar free-syrup.

The fluticasone propionate in the composition may have a $D_{90}$ of less than 10 microns; $D_{90}$ being defined as the diameter where 90% of the particle size distribution has a smaller particle size and 10% a bigger one.

The fluticasone propionate of the invention can be in a crystalline or amorphous form as well as mixture thereof.

The amount of fluticasone propionate in the present invention will be selected so as to maximize the therapeutic benefit depending on the status and age of the patient and severity of the disease and it will be in the range 0.01 mg to 20 mg/dose.

The present invention, in at least one of the aforementioned aspects, can show one or more of the preferred characteristics described below.

The composition of the invention preferably comprises a wetting agent. Suitable wetting agents include sodium lauryl sulfate, docusate sodium, cetylpyridinium chloride, lecithin, poloxamer and polysorbate.

Typically, the ingredients used in the liquid pharmaceutical formulation of the present invention is polysorbate 80 or polysorbate 40.

Preferably, the formulation of the present invention includes an amount of polysorbate between 0.001% and 0.01% w/w relative to the total weight of said pharmaceutical formulation.

The composition of the invention preferably comprises a thickening agent to increase viscosity. Suitable thickening agents include xantan gum, pectins, chitosan derivatives, carrageenan, guar gum, cellulose ethers, povidone, alginic acid, sodium alginate.

Typically, the ingredient used in the formulation of the present invention is sodium alginate. Preferably, the formulation includes an amount of sodium alginate between 0.5% and 10% w/w, depending of the viscosity of the polymer used. Preferably, the formulation includes a sodium alginate with a viscosity of 50-1500 mPas in 1% aqueous solutions.

The composition of the invention preferably comprises also a suspending agent. Suitable suspending agents include cellulose ethers, microcrystalline cellulose and its derivatives, veegum and carbomer.

Typically, the ingredient used in the formulation of the present invention is carbomer. Preferably, the formulation includes an amount of carbomer between 0.1% and 0.5% w/w relative to the total weight of said pharmaceutical formulation.

The composition of the invention preferably comprises a sweetener agent. Suitable sweetener agents include aspartame, cyclamate sodium, cyclamate calcium, acesulfame potassium, sucralose, saccharin sodium, xylitol and sorbitol.

Typically, the ingredient used in the formulation of the present invention is saccharin sodium. Preferably, the formulation includes an amount of saccharin sodium between 0.05% and 0.5% w/w relative to the total weight of said pharmaceutical formulation.

The composition of the invention preferably comprises a preservative system to prevent microbial contamination. Suitable preservatives include chlorobutanol, benzyl alcohol, boric acid, sorbic acid and their respective salts, glycerin, propylene glycol, phenol, chlorocresol, O-phenyl phenol, benzoic acid, and alkyl esters of parahydroxybenzoic acid or mixtures thereof.

Typically, the ingredient used in the formulation of the present invention is a mixture of methyl parahydroxybenzoate and propyl parahydroxybenzoate.

Preferably, the formulation includes an amount of methyl parahydroxybenzoate between 0.05% and 0.5% w/w, more preferably between 0.15 and 0.4%. The formulations include an amount of propyl parahydroxybenzoate between 0.01% and 0.1% w/w relative to the total weight of said pharmaceutical formulation.

The composition of the invention preferably comprises a solid or liquid flavour. such as volatile oils (e.g., orange oil), vanillin, and others, to render the syrup pleasant tasting. These flavors must possess sufficient water-solubility. Typical flavoring agents which are commonly used in sweetened pharmaceuticals, foods, candies, beverages are also useful in the present invention. These materials may impart flavors such as flavor red fruits, green apple, grape, cherry, citrus, peach, strawberry, bubble gum, peppermint and many others and are within the scope of the present invention. Preferred flavoring agents are Flavor Red Fruits and Blood Orange.

Preferably, the formulation includes an amount of flavour between 0.1% and 1% w/w.

The liquid pharmaceutical formulation of the present invention can moreover contain other pharmaceutically acceptable additives conventionally known by a person skilled in the art, for example, antioxidants, buffering agents, chelating agents and colorants.

Useful examples of antioxidants are BHA, BHT, malic acid, ascorbic acid, alpha tocopherol and propyl gallate at the concentration of 0.01-0.1%.

Useful examples of buffering agents are citric acid and citrates of sodium or potassium, phosphoric acid and phosphates of sodium and of potassium. The combination citric acid and sodium citrate is particularly preferred. The amount of buffering agent needed is generally between 0.01 and 0.1 M, and a concentration between 0.05 and 0.5 M is usually sufficient.

In a preferred embodiment, the pH of the liquid pharmaceutical formulation is between about 6 and about 8. Preferably, the pH is between about 6.5 and about 7.5, more preferably the pH is about 7.

The present invention will now be illustrated by the following examples. It is understood, however, that such examples are provided for illustration only, and the invention is not intended to be limited by the examples. The pharmaceutical compositions based on the system employed in the examples can be formed by any suitable method known in the art.

EXAMPLE 1

Pharmaceutical Composition of Fluticasone Propionate Sugar Free Syrup

| Composition | % |
|---|---|
| Fluticasone propionate | 0.01 |
| Sodium alginate | 2.0 |
| Carbomer | 0.1 |
| Saccharin sodium | 0.2 |
| Methyl parahydroxybenzoate | 0.4 |
| Propyl parahydroxybenzoate | 0.06 |
| Blood orange flavour | 0.2 |
| Polisorbate 80 | 0.002 |
| Sodium hydroxide 1M | q.s. |
| Purified water | q.s. to 100 |

Preparation Process of the Suspension

1. Disperse the carbomer into purified water until complete hydratation of the polymer. Neutralize with 1 M Sodium hydroxide (gel formation).
2. Solubilize the propyl parahydroxybenzoate and methyl parahydroxybenzoate into boiling purified water. Add the saccharin sodium.
3. Disperse the fluticasone propionate into purified water at room temperature and add the polysorbate 80 to facilitate the process.
4. Add the API suspension to the preservative solution.
5. Disperse the phase 4 into the phase 1, add the sodium alginate and keep stirring for 40 minutes (mechanical stirring).
6. Add the flavour, bring to pH 6.5-7.5 with sodium hydroxide 1M and add purified water up to final weight.

EXAMPLE 2

Pharmaceutical Composition of Fluticasone Propionate Sugar Free Syrup

| Composition | % |
|---|---|
| Fluticasone propionate | 0.01 |
| Sodium alginate | 3.0 |
| Carbomer | 0.5 |
| Saccharin sodium | 0.2 |
| Methyl parahydroxybenzoate | 0.15 |
| Propyl parahydroxybenzoate | 0.05 |
| Blood orange flavour | 0.2 |
| Polisorbate 80 | 0.002 |
| Sodium hydroxide 1M | q.s. |
| Purified water | q.s. to 100 |

The preparation process is the same of example 1.

EXAMPLE 3

Pharmaceutical Composition of Fluticasone Propionate Sugar Free Syrup

| Composition | % |
|---|---|
| Fluticasone propionate | 0.01 |
| Sodium alginate | 10.0 |
| Saccharin sodium | 0.2 |
| Methyl parahydroxybenzoate | 0.15 |
| Propyl parahydroxybenzoate | 0.05 |
| Mint flavour | 0.2 |
| Polisorbate 80 | 0.002 |
| Sodium hydroxide 1M | q.s. |
| Purified water | q.s. to 100 |

The preparation process is the same of example 1.

EXAMPLE 4

Pharmaceutical Composition of Fluticasone Propionate Sugar Free Syrup

| Composition | % |
|---|---|
| Fluticasone propionate | 0.01 |
| Sodium alginate | 1.0 |
| Cellulose microcristalline and carboxymethylcellulose sodium | 0.5 |
| Saccharin sodium | 0.2 |
| Methyl parahydroxybenzoate | 0.15 |
| Propyl parahydroxybenzoate | 0.05 |
| Blood orange flavour | 0.2 |
| Polisorbate 80 | 0.002 |
| Sodium hydroxide 1M | q.s. |
| Purified water | q.s. |

Preparation Process
1. Disperse cellulose microcristalline and carboxymethylcellulose sodium into purified water until complete hydratation of the polymer.
2. Solubilize the propyl parahydroxybenzoate and methyl parahydroxybenzoate into boiling purified water. Add the saccharin sodium.
3. Disperse the fluticasone propionate into purified water at room temperature and add the polysorbate 80 to facilitate the process.
4. Add the API suspension to the preservative solution.
5. Disperse the phase 4 into the phase 1, add the sodium alginate and keep stirring.
6. Add the flavour, bring to pH 6.5-7.5 with sodium hydroxide 1M and add purified water up to final weight.

EXAMPLE 5

Viscosity of the Free Sugar Syrup

Preparations containing alginates show a typical thixotropic behavior. So, it is important perform the analysis with constant conditions.

Formulations of previous examples show viscosity values between 500 and 5000 mPa·s, depending of type of sodium alginate used. All the analyses were performed with a Brookfield LVT viscometer at 24±0.5° C., with spindle number 2, at 1.5 RPM.

EXAMPLE 6

Stability

The stability of the formulations prepared as described in Examples 1 to 4 was checked for assay, related substances and viscosity after 6 months at room temperature and in accelerated conditions, according to ICH guidelines, and there were no significant changes from initial results.

Microbial testing was also conducted on samples at the beginning of the stability study and after 6 months at 30° C./65% RH. The microbial quality was found to be satisfactory. That is; to have a total aerobic microbial count of not more than 100 bacteria/mL, total molds and yeast count of not more than 10 fungi/mL, and absence of *E. coli, P. aeruginosa, Saureus,* and *Salmonella* sp.

EXAMPLE 7

Adhesion

We tested in vitro, the adhesion properties of our high viscosity formulation versus a regular fluticasone propionate suspension. We compared the formulation of the Example 1, with Flixonase® nasal spray suspension 0.05% (batch n° 1027400051).

Oral use of steroidal suspensions in the form of MDI (meter dose inhaler), DPI (dry powder inhaler), nasal, such as fluticasone propionate (Flixonase®), is suggested as present therapy of eosinophilic esophagitis.

An amount of about 50 mg of both preparations was positioned on a vertical glass surface and the time that the two preparations spend to cover 5 cm at room temperature was measured.

Flixonase suspension spends 5 seconds to cover the distance, while our viscous formulation spends more than 10 minutes.

The results obtained with this simple test suggest that the viscous formulation of the present invention may represent, with its prolonged contact time, an improved alternative to current therapies for eosinophilic esophagitis.

The invention claimed is:
1. A liquid pharmaceutical composition comprising fluticasone propionate in combination with 2.0 wt % of sodium alginate as viscosity enhancer and other non-active ingredients, said non-active ingredients comprising:
   (i) 0.075 wt % of sucralose as edulcorant;
   (ii) 0.1 wt % of carbomer as suspending agent;

(iii) 0.002 wt % of polysorbate 80 as wetting agent surfactant; and
(iv) about 0.2 wt % of a mixture of methylparaben and propylparaben as preservative; and
(v) sodium hydroxide,
wherein the liquid pharmaceutical composition is formulated for oral administration and has a pH between 6.5 and 7.5.

* * * * *

UNITED STATES PATENT AND TRADEMARK OFFICE
CERTIFICATE OF CORRECTION

PATENT NO. : 9,980,975 B2
APPLICATION NO. : 14/603224
DATED : May 29, 2018
INVENTOR(S) : Giancarlo Santus et al.

It is certified that error appears in the above-identified patent and that said Letters Patent is hereby corrected as shown below:

In the Claims

Claim 1 reads as:
A liquid pharmaceutical composition comprising fluticasone propionate in combination with 2.0 wt % of sodium alginate as viscosity enhancer and other non-active ingredients, said non-active ingredients comprising:
    (i) 0.075 wt % of sucralose as edulcorant;
    (ii) 0.1 wt % of carbomer as suspending agent;
    (iii) 0.002 wt % of polysorbate 80 as wetting agent surfactant; and
    (iv) about 0.2 wt % of a mixture of methylparaben and propylparaben as preservative; and
    (v) sodium hydroxide,
    wherein the liquid pharmaceutical composition is formulated for oral administration and has a pH between 6.5 and 7.5.

Should read as:
A liquid pharmaceutical composition comprising fluticasone propionate in combination with 2.0 wt % of sodium alginate as viscosity enhancer and other non-active ingredients, said non-active ingredients comprising:
    (i) 0.075 wt % of sucralose as edulcorant;
    (ii) 0.1 wt % of carbomer as suspending agent;
    (iii) 0.002 wt % of polysorbate 80 as wetting agent;
    (iv) about 0.2 wt % of a mixture of methylparaben and propylparaben as preservative; and
    (v) sodium hydroxide,
    wherein the liquid pharmaceutical composition is formulated for oral administration and has a pH between 6.5 and 7.5.

Signed and Sealed this
Third Day of July, 2018

Andrei Iancu
*Director of the United States Patent and Trademark Office*